(12) United States Patent
Strauss (10) Patent No.: US 8,784,874 B2
(45) Date of Patent: Jul. 22, 2014

(54) MULTI-LAYER TRANSDERMAL DRUG DELIVERY DEVICE

(75) Inventor: Robert C. Strauss, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 2235 days.

(21) Appl. No.: 10/939,163

(22) Filed: Sep. 10, 2004

(65) Prior Publication Data

US 2005/0129749 A1 Jun. 16, 2005

Related U.S. Application Data

(60) Provisional application No. 60/501,709, filed on Sep. 10, 2003.

(51) Int. Cl.
*A61K 9/70* (2006.01)
*A61F 13/00* (2006.01)

(52) U.S. Cl.
USPC .......................... 424/443; 424/447; 424/449

(58) Field of Classification Search
USPC .......................................... 424/443, 447, 449
See application file for complete search history.

(56) References Cited

U.S. PATENT DOCUMENTS

| | | | |
|---|---|---|---|
| 4,390,520 A | 6/1983 | Nagai et al. | |
| 4,559,222 A | 12/1985 | Enscore et al. | |
| 4,584,355 A | 4/1986 | Blizzard et al. | |
| 4,585,836 A | 4/1986 | Homan et al. | |
| 4,591,622 A | 5/1986 | Blizzard et al. | |
| 4,655,767 A | 4/1987 | Woodard et al. | |
| 4,746,515 A | 5/1988 | Cheng et al. | |
| 4,911,707 A | 3/1990 | Heiber et al. | |
| 4,915,950 A | 4/1990 | Miranda et al. | |
| 4,983,395 A * | 1/1991 | Chang et al. | 424/448 |
| 4,994,267 A | 2/1991 | Sablotsky | |
| 4,994,278 A | 2/1991 | Sablotsky et al. | |
| 5,151,271 A | 9/1992 | Otsuka et al. | |
| 5,271,940 A | 12/1993 | Cleary et al. | |
| 5,350,581 A * | 9/1994 | Kochinke | 424/443 |
| 5,446,070 A | 8/1995 | Mantelle | |
| 5,474,783 A | 12/1995 | Miranda et al. | |
| 5,474,787 A | 12/1995 | Grey et al. | |
| 5,505,956 A | 4/1996 | Kim et al. | |
| 5,567,488 A | 10/1996 | Allen et al. | |
| 5,656,286 A | 8/1997 | Miranda et al. | |
| 5,665,377 A | 9/1997 | Gonella | |
| 5,762,952 A | 6/1998 | Barnhart et al. | |
| 5,837,280 A | 11/1998 | Kenealy et al. | |
| 5,902,603 A | 5/1999 | Chen et al. | |
| 5,906,830 A | 5/1999 | Farinas et al. | |
| 5,958,446 A | 9/1999 | Miranda et al. | |
| 6,024,976 A | 2/2000 | Miranda et al. | |
| 6,221,383 B1 | 4/2001 | Miranda et al. | |
| 6,235,306 B1 | 5/2001 | Miranda et al. | |
| 6,562,363 B1 | 5/2003 | Mantelle et al. | |
| 6,808,739 B2 | 10/2004 | Sitz et al. | |
| 2001/0053383 A1 | 12/2001 | Miranda et al. | |
| 2002/0058058 A1 | 5/2002 | Mantelle et al. | |
| 2002/0100185 A1 | 8/2002 | Sitz et al. | |
| 2003/0228354 A1 | 12/2003 | Muraoka et al. | |
| 2005/0169977 A1 | 8/2005 | Kanios et al. | |
| 2006/0078601 A1 | 4/2006 | Kanios et al. | |

FOREIGN PATENT DOCUMENTS

| | | |
|---|---|---|
| AU | 739141 | 10/2001 |
| EP | 1 449 527 A2 | 8/2004 |
| EP | 1 449 527 A3 | 9/2004 |
| WO | WO 91/03998 | 4/1991 |
| WO | WO 93/00058 | 1/1993 |
| WO | WO 00/33812 | 6/2000 |
| WO | WO 01/26705 | 4/2001 |

OTHER PUBLICATIONS

PCT International Search Report for International Application No. PCT/US2004/029789, 5 pages, (Apr. 6, 2005).
Vaughan, "Using Solubility Parameters in Cosmetics Formulation," *J. Soc. Cosmet. Chem.*, vol. 36, pp. 319-333 (1985).
Sobieski et al., "Silicone Pressure Sensitive Adhesives," *Handbook of Pressure-Sensitive Adhesive Technology*. $2^{nd}$ ed., pp. 508-517 (D. Satas, ed.), Van Nostrand Reinhold, New York (1989).
Satas, "Acrylic Adhesives," *Handbook of Pressure-Sensitive Adhesive Technology*, $2^{nd}$ ed., pp. 396-456 (D. Satas, ed.), Van Nostrand Reinhold, N.Y. (1989).
Merck Index, $11^{th}$ Edition, Merck & Co., Rahway, NJ (1980), pp. ther-5 to ther-29.
International Preliminary Report on Patentability and Written Opinion issued Apr. 19, 2007 for application No. PCT/US2005/035805.
"Acrylic and Methacrylic Ester Polymers," *Polymer Science and Engineering*, vol. 1, $2^{nd}$ ed., pp. 234-268, John Wiley & Sons (1984).
Office Action issued on Jun. 11, 2008 in U.S. Appl. No. 10/975,043 (US 2005/0169977).
Office Action issued on Oct. 15, 2008 in U.S. Appl. No. 10/975,043 (US 2005/0169977).
Office Action issued on Jun. 26, 2009 in U.S. Appl. No. 10/975,043 (US 2005/0169977).
Office Action issued on Jun. 10, 2009 in U.S. Appl. No. 11/245,084 (US 2006/0078601).
Office Action issued on Oct. 13, 2010 in U.S. Appl. No. 10/975,043 (US 2005/0169977).
Office Action issued on Feb. 3, 2010 in U.S. Appl. No. 10/975,043 (US 2005/0169977).
Office Action issued on Apr. 14, 2010 in U.S. Appl. No. 11/245,084 (US 2006/0078601).

\* cited by examiner

*Primary Examiner* — Frederick Krass
*Assistant Examiner* — Tracy Liu
(74) *Attorney, Agent, or Firm* — Foley & Lardner LLP (57) ABSTRACT

A drug delivery device initially having two adhesive layers containing at least one active agent in each layer are kept separate from each other prior to administration of the active agent. At the time of administration, the separated layers are combined to form a dual layer adhesive transdermal drug delivery device which results in the administration of the at least one active compound after topical application of the device.

19 Claims, 3 Drawing Sheets

MULTI-LAYER TRANSDERMAL DRUG DELIVERY DEVICE

RELATE BACK

This application claims the benefit of U.S. Provisional Application No. 60/501,709 filed Sep. 10, 2003.

TECHNICAL FIELD

This invention relates generally to transdermal drug delivery systems, and more particularly, to delivery systems for continuous and controlled delivery of active agents over a prolonged period of time. The delivery system comprises at least two separate layer assemblies, which are combined prior to application to form a single, multi-layer transdermal drug delivery device. The multi-layer delivery device is designed to allow an active agent in each of the assemblies to be controllably released, or to allow different active agents to be delivered.

BACKGROUND OF THE INVENTION

The use of transdermal drug delivery systems as a means to topically administer an active agent is well known. Such systems incorporate the active agent into a carrier composition, such as a polymeric and/or pressure-sensitive adhesive composition, from which the active agent is delivered through the skin or mucosa of the user.

In general, transdermal drug delivery systems are either reservoir-type or matrix-type. Both types of systems have generally included a backing layer that forms the protective outer surface of the finished transdermal device and which is exposed to the environment during use, and a release liner or protective layer that forms the inner surface and which covers the adhesive layer for affixing the device to the skin or mucosa of a user. The release liner or protective layer is removed prior to application, exposing the adhesive layer, which is typically a pressure-sensitive adhesive. The active agent is located between the release liner and backing layer, usually solubilized or dispersed in a solvent or carrier composition.

In a reservoir-type device, the active agent, typically in fluid or gel form, is isolated from the adhesive layer used to affix the device to the user. Traditionally, a reservoir system referred to a device having a pocket or "reservoir" which served to hold the active agent and which was formed in or by the backing layer itself. A peripheral adhesive layer was then used to affix the device to the user. While such devices are still in use today, the term reservoir has become known as a device which employs one or more permeable layers, such as rate controlling membranes and drug permeable adhesives layers, laminated over the reservoir (which is typically nothing more than another layer containing the drug in a carrier composition), in order to more effectively control the delivery rate of the active agent and attachment of the device to the user.

A matrix-type device generally comprises the active agent solubilized or dispersed in an adhesive carrier composition, typically a pressure-sensitive adhesive or bioadhesive, which functions as both the drug carrier and the adhesive means of applying the system to the skin or mucosa.

A transdermal device has particular advantages over other forms of drug delivery, such as oral administration, in that the transdermal system can provide a continuous and controlled release of an active agent over a prolonged period of time, so that the resulting blood levels remain at a desired level throughout treatment. In this regard, different active agents have differing release characteristics, depending on the agent itself, as well as the matrix material it is disposed in. Further, depending on the treatment program, the desired delivery rate may be different over the treatment period. Known transdermal delivery systems in general are designed to provide constant delivery of the agent and cannot provide multiple delivery rates or varying rates over a treatment period.

As the agent is typically disposed in a single carrier composition, the delivery rate is controlled by the degree of saturation and solubility of the active agent in the carrier composition. Generally, active agents have been found to be readily soluble in acrylic polymers. However, in order to deliver a therapeutically effective amount to the system's user, and to also achieve the desired adhesive strength required for topical application in a matrix-type system, additional polymers and ingredients are often added to the carrier composition (for example, incorporating a rubber, polysiloxane or polyvinylpyrrolidone polymer).

Formulation of transdermal systems is further frequently hampered by poor solubility of certain active agents in the carrier composition, which in turn also severely limits its therapeutic application. This formulating aspect is particularly difficult in matrix-type systems because the carrier composition has to be optimized not only for the desired active agents but also for the carrier's pressure-sensitive adhesive properties. While using low concentrations in order to incorporate the active agent into the carrier may not deleteriously affect the carrier's adhesive properties, low active agent concentration can result in difficulties in achieving an acceptable delivery rate.

Generally, concentrations of the active agent up to the saturation solubility, and even supersaturated (i.e., an amount of active agent at a concentration greater than the solubility of the active agent in the carrier composition at room temperature) are sought in order to increase or maximize delivery rates. Such systems also allow for continuous administration of the active drug in therapeutically effective amounts for prolonged periods of time, such as greater than 24 hours, and even up to 7 days or more. In such systems, however, the delivery rate is again controlled by the characteristics of the carrier material, and the balance between retaining the desired adhesive qualities along with delivery of the active agent can result in less than optimum overall characteristics.

To adjust the delivery rate of such systems, attempts have been made to utilize a rate controlling membrane. Combinations of matrix reservoirs with rate-controlling membranes have also been proposed. The typical design criteria are to provide a substantially constant and continuous release rate, and to provide a release rate capable of delivering a therapeutically effective amount of the compound. More recently, dual layer transdermal delivery systems have been developed. In these systems, a drug-containing polymer adhesive layer and a second chemically distinct polymer adhesive layer not having any drug therein, are positioned adjacent one another. The second layer is applied to the skin, and is suggested as providing a rate controlling structure for controlling migration of the drug from the first layer to the skin. Alternatively in these systems, a rate controlling membrane is typically used in order to mediate the delivery of the drug from the first layer through the second layer. One problem with this system is that upon storage, the drug from the first layer can equilibrate into the second layer creating an undesirable and potentially harmful situation.

There is a need in the art for transdermal drug delivery devices in which two separate active agent-containing layers are combined prior to application to form a single, multi-layer adhesive transdermal drug delivery device. A need exists for a device of this character that allows different release rates from each layer, and the ability to deliver different concentrations and/or different agents to a user.

The drug delivery devices of the type as described above also do not allow a great amount of flexibility in effectively controlling the release rate of a drug through the patients skin from the device. The use of rate controlling membranes, or a drug-free adhesive layer in the dual layer devices provides a single release rate from the entire system. It would be desirable to provide a delivery device which allowed different release rates to be achieved for the delivery of one or more active agents through the patient's skin.

SUMMARY OF THE INVENTION

It is therefore an object of the invention to provide a multilayer transdermal delivery system which overcomes the limitations of the prior systems and provides the desirable features of providing two or more types of drugs or other agents to a patient simultaneously, each with a predetermined flux rate for providing the amount of a particular agent as desired over a treatment period. The invention is directed to a device having the ability to provide different concentrations, different release rates, different active agents and combinations of these variables to provide distinct advantages and flexibility in manufacturing and design.

The present invention is directed to a device for delivering at least one active compound to a subject's epidermis comprising at least a first layer assembly and a second layer assembly, each having a first and a second face and containing at least one active compound. At least one of the layer assemblies is capable of being selectively adhesively adhered to another of the layer assemblies and/or to a user's epidermis. The first layer assembly and the second layer assembly are initially separated from each other to maintain characteristics of the assemblies until use is desired. For use, a face of the first layer assembly and a face of the second layer assembly are combined prior to application to a subject's epidermis to form a monolithic device adapted to deliver said at least one active compound from the first layer assembly and said at lest one active compound from the second layer assembly. The device is capable of delivering different concentrations of a common active agent or a plurality of active agents, and accomplishes delivery of an active compound or active compounds at a desired delivery rate or rates. It is also an object to provide a delivery device which allows different release rates to be achieved from multiple layer configurations.

In alternate embodiments of the present invention, a plurality of first layer assemblies is provided, and corresponding thereto is at least one second layer assembly. the plurality of first assemblies are separated from one another and from the at least one second assembly until use is desired, and are combined into a monolithic device for use. At least one of the first assemblies and the at least one second assembly each contain at least one active compound and each has a predetermined first release rate for the at least one active compound. The first and second layer assemblies may have the same or different active agents or compounds, having same or different concentrations. The release rates of each assembly having an active agent may be varied for function in the monolithic device in a selected manner.

For a better understanding of the present invention, together with other and further objects thereof, reference is made to the following description, taken in conjunction with the accompanying drawings, and its scope will be pointed out in the appending claims.

DETAILED DESCRIPTION OF THE PRESENT INVENTION

In the following description, embodiments of the invention are set forth, and terms are used in describing such embodiments, wherein:

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage of an active agent into and/or through skin or mucosa for localized or systemic delivery.

The term "solubilized" is intended to mean that in the carrier composition there is an intimate dispersion or dissolution of the active agent at the crystalline, molecular or ionic level, such that crystals of the active agent cannot be detected using a microscope having a magnification of 25×. As such, the active agent is considered herein to be in "non-crystallized" form when in the compositions of the present invention.

As used herein, the term "flux" is defined as the absorption of the drug through the skin or mucosa, and is described by Fick's first law of diffusion:

$$J = -D(dCm/dx),$$

Where J is the flux in g/cm2/sec, D is the diffusion coefficient of the drug through the skin or mucosa in cm2/sec and Dcm/dx is the concentration gradient of the drug across the skin or mucosa.

As used herein, "therapeutically effective" means an amount of an active agent that is sufficient to achieve the desired local or systemic effect or result, such as to prevent, cure, diagnose, mitigate or treat a disease or condition, when applied topically over the duration of intended use. The amounts necessary are known in the literature or may be determined by methods known in the art, but typically range from about 0.1 mg to about 20,000 mg, and preferably from about 0.1 mg to about 1,000 mg, and most preferably from about 0.1 to about 500 mg per human adult or mammal of about 75 kg body weight per 24 hours.

The term "carrier" as used herein refers to any non-aqueous material known in the art as suitable for transdermal drug delivery administration, and includes any polymeric material into which an active agent may be solubilized in combination or admixture with the other ingredients of the composition such as polyacrylate and polysiloxane polymers and rubbers such as polyisobutylene. The polymeric materials preferably comprise adhesives and, in particular, pressure-sensitive adhesives. The carrier material is typically used in an amount of about 10% to about 90%, and preferably from about 10% to about 75%, by weight based on the dry weight of the total carrier composition.

The term "carrier composition" may also refer to enhancers, solvents, co-solvents and other types of addictives useful for facilitating transdermal drug delivery.

The carrier compositions of the present invention can also contain one or more solvents and/or co-solvents. Such solvents and/or co-solvents are those known in the art, and are non-toxic, pharmaceutically acceptable substances, preferably liquids, which do not substantially negatively affect the adhesive properties or the solubility of the active agents at the concentrations used. The solvent and/or co-solvent can be for the active agent or for the carrier materials, or both.

Suitable solvents include volatile liquids such as alcohols (e.g., methyl, ethyl, isopropyl alcohols and methylene chloride); ketones (e.g., acetone); aromatic hydrocarbons such as benzene derivatives (e.g., xylenes and toluenes); lower molecular weight alkanes and cycloalkanes (e.g., hexanes, heptanes and cyclohexanes); and alkanoic acid esters (e.g., ethyl acetate, n-propyl acetate, isobutyl acetate, n-butyl acetate isobutyl isobutyrate, hexyl acetate, 2-ethylhexyl acetate or butyl acetate); and combinations and mixtures thereof.

Suitable co-solvents include polyhydric alcohols, which include glycols, triols and polyols such as ethylene glycol, diethylene glycol, propylene glycol, dipropylene glycol, trimethylene glycol, butylene glycol, polyethylene glycol, hexylene glycol, polyoxethylene, glycerin, trimethylpropane, sorbitol, polyvinylpyrrolidone, and the like.

Further suitable co-solvents include glycol ethers such as ethylene glycol monoethyl ether, glycol esters, glycol ether esters such as ethylene glycol monoethyl ether acetate and ethylene glycol diacetate; saturated and unsaturated fatty acids, mineral oil, silicone fluid, lecithin, retinol derivatives and the like, and ethers, esters and alcohols of fatty acids.

In certain embodiments of the invention, an enhancer is incorporated into the carrier composition. The term "enhancers" as used herein refers to substances used to increase permeability and/or accelerate the delivery of an active agent through the skin or mucosa, and include monhydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearly) including polyoxyethylene (4) lauryl ether, polyoxyethylene (2) oleyl ether and polyoxyethylene (10) oleyl ether commercially available under the trademark BRIJ® 30, 93 and 97 from ICI Americas, Inc., and BRI® 35, 52, 56, 58, 72, 76, 78, 92, 96, 700 and 721; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered and esters of sorbitol and sorbitol anhydride such as polysorbate 20 commercially available under the trademark Tween® 20 from ICI Americas, Inc., as well as other polysorbates such as 21, 40, 60, 61, 65, 80, 81, and 85. Other suitable enhancers include oleic and linoleic acids, triacetin, ascorbic acid, panthenol, butylated hydroxytoluene, tocopherol, tocopherol acetate, tocopheryl linoleate. If enhancers are incorporated into the carrier composition, the amount typically ranges up to about 30%, and preferably from about 0.1% to about 15%, by weight based on the dry weight of the total carrier composition.

In addition to enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenes, silicone fluid, mineral oil and hydrogenated wood rosins. Additional additives include binders such as lecithin which "bind" the other ingredients, or rheological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the final composition. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the carrier composition. Such additives or excipients are typically used in amounts up to 25%, and preferably from about 0.1% to about 10%, by weight based on the dry weight of the total carrier composition.

The term "about", and the use of ranges in general whether or not qualified by the term about, means that the number comprehended is not limited to the exact number set forth herein, and is intended to refer to ranges substantially within the quoted range not departing from the scope of the invention.

The term "user" or "subject" is intended to include all warm-blooded mammals, preferably humans.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

Figure 1:
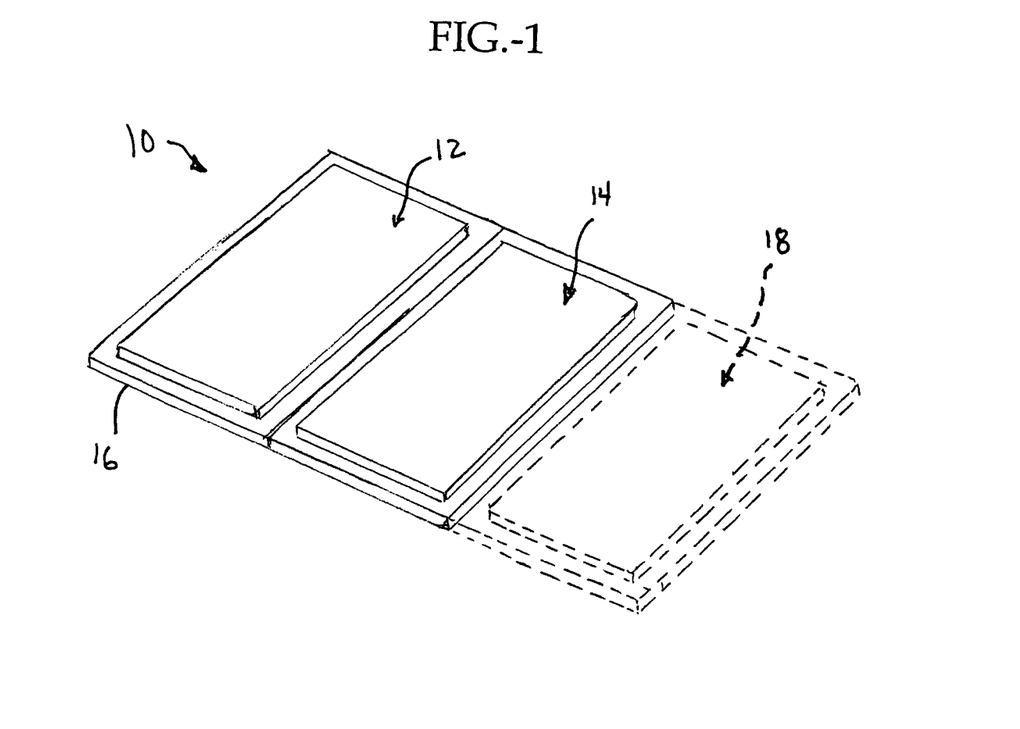
FIG. 1 shows a perspective view of a transdermal drug delivery device according to an embodiment of the invention prior to use, with a portion thereof removed for clarity.
Figure 2:
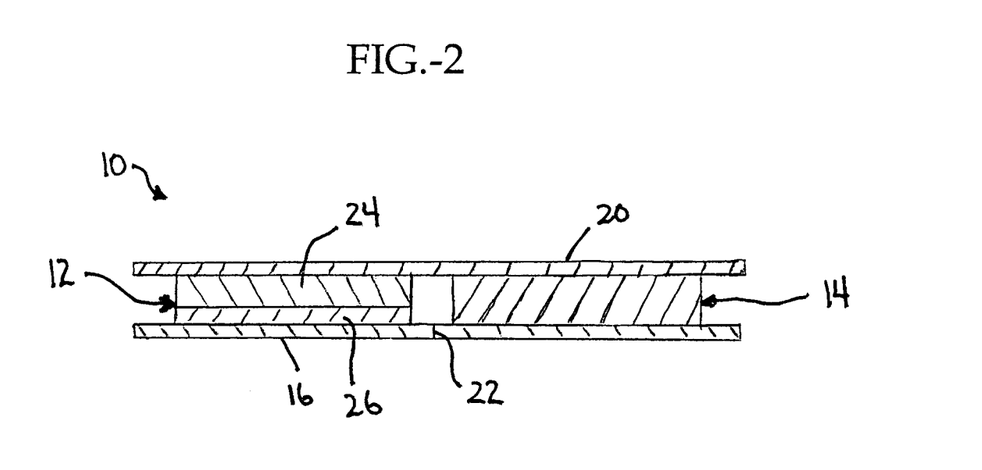
FIG. 2 shows a schematic cross-section of the embodiment of the present invention as shown in FIG. 1.

Referring to FIG. 1, a drug delivery system 10 according to an embodiment of the invention is shown. In this embodiment, the assemblies 12 and 14 may each comprise a matrix composition having an active agent solubilized or dispersed in a carrier composition. The matrix-type assemblies 12 and 14 include at least one having a pressure-sensitive adhesive or bio-adhesive carrier composition to provide means for applying the system to the skin or mucosa. One or more further assemblies 18 may be provided to facilitate in the delivery of active agents or as an adhesive means of applying the system to the skin or mucosa. The assemblies 12 and 14 may thus be formulated in any desired composition for providing desired attributes in the device 10. As seen in FIG. 2, a further release liner 20 may be provided on the upper side of device 10 to protect assemblies 12 and 14. The release liner 20 has been removed from FIG. 1 for clarity. Separating the assemblies 12 and 14, the release liner 16 may have a fold line 22, to facilitate subsequent assembly of device 10, as will be hereinafter described. In the embodiment as shown in FIG. 2, the assembly 12 may include a matrix layer 24 or a reservoir type device including one active agent, and a backing layer 26. The backing layer 26 forms the protective outer surface of the finished transdermal device 10, which when worn by a subject, is exposed to the environment during use.

Figure 3:
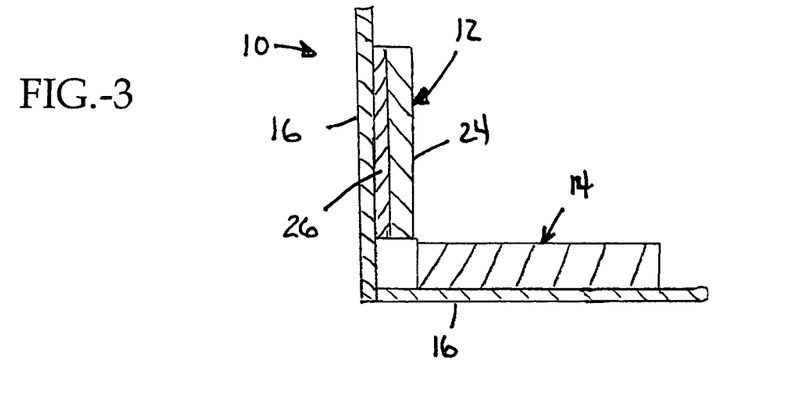
FIG. 3 shows a schematic view of the assembly of the embodiment of the present invention as shown in FIG. 1.
Figure 4:
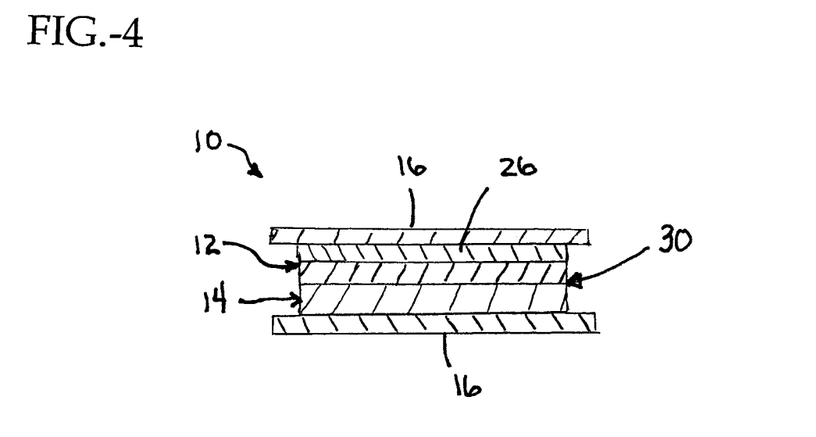
FIG. 4 shows a schematic cross section of the assembled embodiment of the present invention showing a transdermal delivery device ready for use.

As seen in FIGS. 3 and 4, the device 10 is designed to allow assemblies 12 and 14 to be integrated into a single system 30, which is subsequently applied to a subject's body. As seen in FIG. 3, the release liner 20 is removed, exposing the matrix composition 24 of assembly 12, as well as of assembly 14. Folding the assemblies 12 and 14 upon one another, the assemblies are registered to one another to form monolithic body 30. The release liner 16 still covers the other surface of assembly 14, and is also removably adhered to backing layer 26. The release liner 16, although shown as being separated in the form of FIG. 4, may be of any configuration to allow assemblies 12 and 14 to be combined into monolithic body 30. If one or more further assemblies 18 are provided in the device 10, the assemblies may be configured to allow combination of the multiple assemblies into at least one monolithic body 30 for application to a subject's body. The release liner 16 provides a protective layer which covers the at least one assembly having adhesive characteristics for affixing the device to the skin or mucosa of a user. The release liner 16 may be removed prior to application, exposing he adhesive means, such as a pressure-sensitive adhesive or bio-adhesive. The liner 16 may also be removed from the backing layer 26, such that only the monolithic body 30 is applied to a user.

By providing a plurality of assemblies 12, 14 and 18, which are separated from one another prior to use, each of the assemblies 12, 14 and 18, etc., can be configured with specific characteristics for performing a predetermined function in the final one or more monolithic bodies 30 of device 10. Each of the assemblies 12 and 14 may include at least one active agent solubilized or dispersed within at least a portion of the assembly. Upon subsequent combination of assemblies into monolithic body 30, the selected characteristics of the assemblies 12, 14, 18, etc., produce combined functions in a desired manner, to provide delivery of the agents to the user. The carrier compositions of the assemblies 12 and 14 (and possibly others) are chosen to provide certain defined characteristics in the finished device 10.

Selection of the particular carrier composition is governed in large part by the desired rate of delivery of the drug. Those skilled in the art can readily determine the rate of drug delivery from the transdermal composition in order to select a suitable polymer or combination of polymers and/or other materials for a particular application. Combinations of polymers based on their differing solubility parameters can be used, such as those described in U.S. Pat. Nos. 4,994,267; 5,446,070; 5,474,783; 5,656,286; 6,024,976; 5,958,446; 6,221,383; 6,235,306; 6,316,022; 6,465,004; and 6,562,363 all of which are assigned to Noven Pharmaceuticals, Inc., Miami, Fla., and which are expressly incorporated by reference in their entirety. Various techniques can be used to determine the rate of delivery of the drug from the polymer matrix. Illustratively, the rate of delivery can be determined by measuring the transfer of the selected drug from one chamber to another through cadaver skin over time, and calculating, from the obtained data, the drug delivery or flux rate.

By providing multiple assemblies 12, 14, 18, etc., each of the assemblies can be tailored to perform a specific function or functions upon use by a subject. In this regard, the assemblies 12, 14, etc., can be made to have different concentrations or strengths of a common active agent, to provide controlled flux response in final device 10 or to vary the flux rate over a treatment period. Although not shown in the embodiment of FIG. 2. The assemblies 12 and 14, etc., may also be provided with additional materials or structures to provide desired function in the finished device 10. For example, rate controlling membranes or barriers to segregate active agents or the like within an assembly may be used. Similarly, although shown as a matrix-type composition, the assemblies 12, 14 or others may comprise a reservoir type of device for use in the combination finish device 10. As an alternative to providing a common active agent via multiple assemblies, the invention also contemplates the delivery of more than one active agent via the finished device 10. Individual assemblies 12, 14 or others may thus include differing active agents, or using barrier structures or the like, multiple active agents may be provided in a single assembly. For example, using the multiple assemblies according to the invention, a first type of drug may be incorporated into one of the assemblies 12 and 14, while an anesthetic or other active agent could be provided in the other assembly, such that upon being combined, both fast acting and long acting effects may be achieved in controlling pain or the like. It may also be desirable to provide two types of drugs to a patient simultaneously, each with a predetermined flux rate for providing the amount of a particular drug as desired over a treatment period. Thus, the ability to provide different concentrations, different release rates, different active agents and combinations of these variables in a device 10 provides distinct advantages and flexibility in manufacturing and design. For example, as each of the assemblies 12, 14 or others may not require the capability to serve as an adhesive layer, it may be possible to optimize the drug delivery characteristics of an assembly. Similarly, an assembly may also serve as an adhesive means, wherein the active agent is provided in a manner so as to not significantly impair the adhesive characteristics thereof.

The amount of active agent to be incorporated into the carrier composition of assemblies 12, 14 or others depends upon the particular active agent, the desired therapeutic effect, and the time span for which the transdermal system is to provide therapy. Thus, any suitable amount of active agent to accomplish these objectives may be used, and is contemplated, such as varying from about 0.1% to about 50% by weight, based upon the dry weight of the total carrier composition.

The term "active agent" (and its equivalents "agent," "drug," "medicament" and "pharmaceutical") is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. It should be noted that the active agents can be used singularly or in combinations and mixtures. Within the contemplation of the term are such agents as insect repellents, sun screens, cosmetic agents, etc. It should be noted that the agents may be used singly or as a mixture of two or more such agents, and in amounts sufficient to prevent, cure, diagnose or treat a disease or other condition, as the case may be. A therapeutically effective amount as used herein is intended to mean the amount of agent sufficient to produce the desired effect, local or systemic, over the duration of intended use of the transdermal patch. There is no limitation on the type of agents that can be used in this invention.

The active agents contained in the carrier composition can be in different forms depending on the solubility and release characteristics desired, for example as neutral molecules, components of molecular complexes, and pharmaceutically acceptable salts, free acids or bases, or quaternary salts of the same. Simple derivatives of the drugs such as pharmaceutically acceptable ethers, esters, amides and the like which have desirable retention and release characteristics but which are easily metabolized at body pH, and enzymes, pro-active forms, pro-drugs and the like, can also be employed.

To allow attachment to a subject's body, at least one of the one assemblies 12, 14 or others, provides an adhesive means, such as a pressure-sensitive adhesive, forming an adhesive polymer system. An "adhesive" as used herein means any natural or synthetic substance that is capable of surface attachment to the topical site of the transdermal drug delivery system. As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizer or other additives. The term pressure-sensitive adhesive also includes mixtures of different polymers and mixtures of polymers, such as polyisobutylenes (PIB) of different molecular weights, the resultant mixtures being a pressure-sensitive adhesive. In the last case, the polymers of lower molecular weight in the mixture are not considered to be "tackifiers," said term being reserved for additives which differ other than in molecular weight from the polymers to which they are added.

The adhesive polymer system is preferably formulated so that it is a pressure-sensitive adhesive at or about room temperatures and has other desirable characteristics for adhesives used in the transdermal drug delivery art. Such characteristics include good adherence to skin, ability to be peeled or otherwise removed without substantial trauma to the skin, retention of tack with aging, etc. In general, the adhesive polymer system should have a glass transition temperature ($T_g$), measured using a differential scanning calorimeter, of between about 70 C. and 0 C.

In a particularly preferred embodiment, the adhesive polymer system comprises an acrylic-based and/or silicone-based polymer. Suitable acrylic adhesives are commercially available and include the polyacrylate adhesives sold under the trademarks Duro-Tak® 87-2194, -2196, -2296, -2097, -2287, -2516, -2852, -4194, -9082, -9085, and -9088 by National Starch and Chemical Corporation, Bridgewater, N.J. Other suitable acrylic adhesives are those sold under the trademarks Gelva® Multipolymer Solution 737, 788, 1151, 1430, 1753, 2480, 2495, and 3087 (UCB Surface Specialties, Smyrna, Ga.). Still other suitable acrylic adhesives are those sold under the trademark Morstik 703, 707, 705, 607, 709 and 605, all available from Morton International Corporation. Suitable polysiloxane adhesives include those commercially available from Dow Corning Corporation, Midland, Mich., and sold under their BIO-PSA® -4100, -4200, -4300, -4400, -4500 and -4600 product series including -4102, -4201, -4203, -4302, -4402, -4403, -4502, -4503, and -4602.

In the present invention, a plurality of polymers having differing solubility parameters may be blended (but not chemically reacted or cross-linked) resulting in a pressure-sensitive adhesive composition, or transdermal drug delivery system adhesive system (with incorporated drug), which controls delivery of an incorporated drug into and through the epidermis. The blending of polymers results in an adjustment of the saturation concentration of the drug in the polymeric system and therefore permits selective modulation of the transdermal drug delivery rate. The term "blending," of course, incorporates choosing the appropriate polymeric components, and the proportions thereof, to achieve the desired effect.

In a device 10 of the invention, the preferred pressure-sensitive adhesive composition embodiment can be used as an adhesive portion of any transdermal delivery system 10 (e.g., a reservoir device) or an adhesive monolithic device. The principles of the invention would still apply to embodiments where the transdermal drug delivery composition is not a pressure-sensitive adhesive and comprises a drug reservoir.

The assemblies 12, 14 and 18 forming device 10, or individual dosage unit, of the present invention, can be produced in any manner known to those of skill in the art. After the dermal composition is formed, it may be brought into contact with the backing layer in any manner known to those of skill in the art. Such techniques include calender coating, hot melt coating, solution coating, etc. The backing layer 26 may be constructed of materials that are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Dow Corning Corporation designated Bio-Releases liner and Syl-off® 7610 liner. For preferred embodiments in which a polysiloxane is part of the multiple polymeric adhesive system, the release liner must be compatible with the silicone adhesive. An example of a suitable commercially available liner is 3M's 1022 Scotch Pak.

To use the device 10, the release liner 20 is first removed from the upper surface of the device 10 exposing the first face of assemblies 12 and 14. The exposed first face of assembly 12 is then combined with the exposed first face of assembly 14. The fold line 22 and position of assemblies 12 and 14 relative thereto, ensures that the completed device layers will properly register and overlap completely. Upon forming the final configuration shown in FIG. 4, and applying the device 10 to the skin of mucosa, active compounds in assemblies 12 and 14 begin diffuse into the subject's epidermis. Prior to formation of finished device 10 as shown in FIG. 4, the separation of assemblies 12, 14 or others prevents migration of active agents from individual assemblies and also prevents equilibration of active compounds between assemblies.

The drug delivery device of this invention can be of any suitable shape, including square, rectangular, circular, oval, or irregularly shaped. Providing at least two assemblies 12 and 14 having an active agent therein may also be supplemented by additional assemblies 18 as previously described. The use of additional assemblies 18 may provide similar abilities to assemblies 12 and 14 in conjunction therewith and may also allow assemblies 12 and 14 to be formulated to provide a desired flux in association with at least one active agent, while a further assembly 18 could be used as the adhesive system for adhering the finished device 10 to the skin or mucosa. In this manner, assemblies 18 may not include further active agents, but may provide the adhesive system for attachment of the device 10 to the skin or mucosa. Alternatively, additional assemblies 18 may be provided as a rate-controlling member which in conjunction with the other assemblies 12 and 14, provide desired flux rate of active agents therefrom. The formulation of assembly 18 may also provide for differing rate controlling functions over different portions thereof, by suitable modification of the formulation of the material making up assembly 18. As should be recognized, assemblies 12, 14, 18 and potentially others, may be configured so as to include an active agent only over a portion thereof, such that delivery of an active agent occurs from only that portion. In combination with one another, varying delivery of active agents or flux rates for the active agents may be effectively controlled to provide desired function over a therapy.

Figure 5:
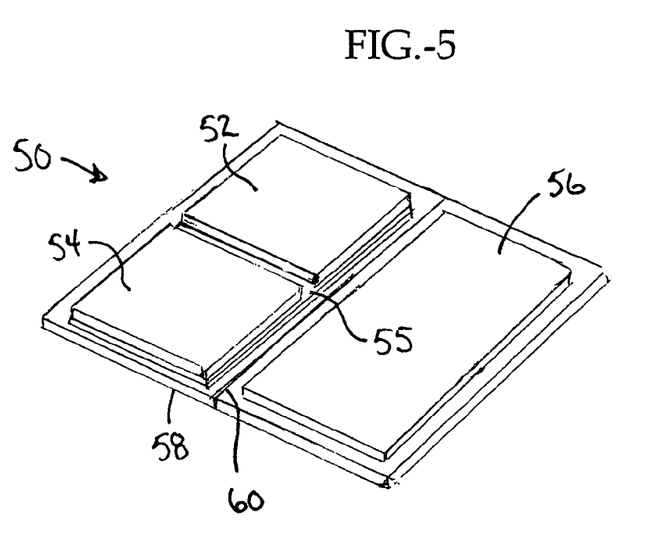
FIG. 5 shows a schematic perspective view of an alternate embodiment of the invention.
Figure 6:
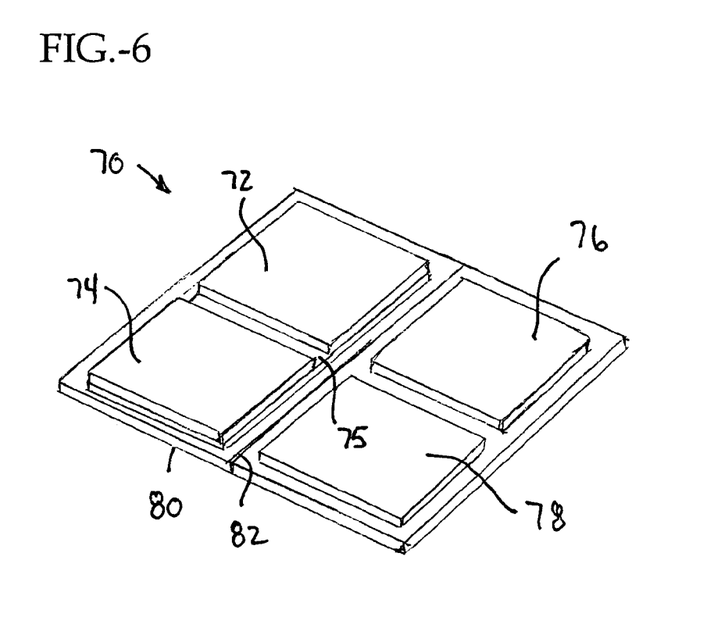
FIG. 6 shows a schematic perspective view of another embodiment of the invention.

Turning now to FIG. 5, an alternate embodiment of the invention shows a device 50 having first and second assemblies 52 and 54, which may be similar to assemblies 12, 14, 18 etc., as previously described, disposed over a portion of a bottom release liner 58. A further assembly 56 may be disposed over another portion of release liner 58 in relationship to assemblies 52 and 54. A fold line 60, similar to the previous embodiment, allows for folding of the release liner 58 so as to laminate assemblies 52 and 54 to assembly 56. In such an embodiment, assemblies 52 and 54 may be provided with distinct characteristics, which upon combination with assembly 56, allow desired delivery of one or more agents to the skin or mucosa of a subject. The assemblies 52 and 54 may be carried on a common backing layer 55, such that upon combination with assembly 56, allows simplified application to the skin or mucosa as an integral unit. Providing a plurality of assemblies 52 and 54 in conjunction with a common assembly 56 maintains each of the assemblies in a separate condition until being combined for use, after which desired delivery of agents to a user in a desired manner. Similarly, as shown in FIG. 6, an embodiment of the device 70 may include plural assemblies 72 and 74 disposed on a portion of release liner 80, as well as a plurality of assemblies 76 and 78 disposed on another portion of release liner 80. A fold line 82 may again be used to facilitate a subsequent combination of assemblies to one another in a desired manner for use. In the embodiment shown, assembly 72 will be combined with assembly 76, while assembly 74 will be combined with assembly 78. If desired, a plurality of assemblies may be provided with a common backing layer 75, to facilitate subsequent application by a user. In this embodiment, it again should be recognized that individual characteristics of assembly 72, 74, 76 and 78 are subsequently selectively combined to provide distinct functions in the finished device 70. It is contemplated that any of the various embodiments as described previously may be utilized in the embodiments of FIGS. 5 and 6, or various alternative embodiments as can be envisioned by practitioners. Thus, it is contemplated that a wide variety of alternative configurations wherein a plurality of assemblies are used to provide discreet functions in a combined device are within the scope of the invention. It is again possible in these embodiments to maintain the assemblies in a separate condition until use, to preserve the characteristics to be provided by the assemblies upon use of the device.

Although the invention has been described and illustrated with respect to certain preferred embodiments, it should be understood that the description is for illustration and example only, and is not meant to limit the spirit and scope of this invention.

What is claimed is:

1. A multi-layer transdermal delivery system comprising:
a first layer assembly and a second layer assembly, each having a first face and a second face and each containing a therapeutically effective amount of at least one systemically pharmaceutically active agent; wherein:
said first layer assembly is capable of being selectively adhesively adhered to said second layer assembly, which is capable of being selectively adhesively adhered to a user's epidermis;
said first layer assembly and said second layer assembly are separate from each other to maintain characteristics of the assemblies until use;
said first layer assembly comprises (i) a first face release liner adhered to said first face, (ii) a backing layer adhered to said second face; and (iii) a second face release liner adhered to said backing layer;
said second layer assembly comprises (i) a first face release liner adhered to said first face and a (ii) a second face release liner adhered to said second face, and does not include a backing layer; and
said first face of said first layer assembly and said first face of said second layer assembly are adapted to be applied to each other, upon removal of said first face release liner(s), and prior to use, to form a single multi-layer system wherein said first and second layer assemblies are arranged vertically with respect to one another.

2. The transdermal delivery system of claim 1, wherein the at least one systemically pharmaceutically active agent in each of the first and second assemblies is the same agent.

3. The transdermal delivery system of claim 2, wherein the at least one systemically pharmaceutically active agent in each of the first and second assemblies is present in different concentrations.

4. The transdermal delivery system of claim 1, wherein the at least one systemically pharmaceutically active agent in each of the first and second assemblies is a different pharmaceutically active agent.

5. The transdermal delivery system of claim 1, wherein the at least one systemically pharmaceutically active agent in each of the first and second assemblies is delivered at a selected delivery rate from each of the assemblies.

6. The transdermal delivery system of claim 5, wherein the delivery rate of the at least one systemically pharmaceutically active agent from each of the assemblies is different.

7. The transdermal delivery system of claim 5, wherein the delivery rate of the at least one systemically pharmaceutically active agent from each of the assemblies is selected such that during use of the single multilayer system, the at least one systemically pharmaceutically active agent is provided at a selected delivery rate from said single multilayer system.

8. The transdermal delivery system of claim 5, wherein each of the first and second assemblies comprises at least two systemically pharmaceutically active agents, and the delivery rate from each of the assemblies is selected such that during use of the single multilayer system, the systemically pharmaceutically active agents are provided at a selected delivery rate from said single multilayer system.

9. The transdermal delivery system of claim 1, wherein the first and second layer assemblies are formed as matrix or reservoir devices.

10. The transdermal delivery system of claim 1, comprising:

a plurality of first layer assemblies capable of being selectively adhered to at least one second layer assembly, and
at least one second layer assembly,
wherein said first face of each of said first layer assemblies is adapted to be applied to a first face of at least one of said at least one second layer assembly to form said single multi-layer system.

11. The transdermal delivery system of claim 1, comprising a single second face release liner adhered to both said backing layer of said first layer assembly and said second face of said second layer assembly.

12. The transdermal delivery system of claim 11, wherein said second face release liner further comprises a fold line facilitating the folding of the liner to facilitate the application of said first face of said first layer assembly to said first face of said second layer assembly to form said single multi-layer system.

13. The transdermal delivery system of claim 1, comprising a single first face release liner adhered to both said first face of said first layer assembly and said first face of said second layer assembly.

14. The transdermal delivery system of claim 10, comprising a plurality of first layer assemblies and one second layer assembly.

15. The transdermal delivery system of claim 10, comprising a plurality of first layer assemblies and a plurality of second layer assemblies.

16. A transdermal delivery system for delivering at least one systemically pharmaceutically active agent transdermally comprising:
a first layer assembly having a first face and a second face and containing a therapeutically effective amount of at least one systemically pharmaceutically active agent, wherein said first layer assembly has a first release rate for said at least one systemically pharmaceutically active agent; and
a second layer assembly having a first face and a second face and containing a therapeutically effective amount of at at least one systemically pharmaceutically active agent, wherein said second layer assembly has a second release rate for said at least one systemically pharmaceutically active agent;
wherein said first and second release rates are different;
wherein said first layer assembly is capable of being selectively adhesively adhered to said second layer assembly, which is capable of being selectively adhesively adhered to a user's epidermis;
wherein said first layer assembly and said second layer assembly are separate from each other to maintain characteristics of the assemblies until use;
wherein said first layer assembly comprises (i) a first face release liner adhered to said first face, (ii) a backing layer adhered to said second face; and (iii) a second face release liner adhered to said backing layer;
wherein said second layer assembly comprises (i) a first face release liner adhered to said first face and a (ii) a second face release liner adhered to said second face, and does not include a backing layer; and
wherein said first face of said first and second layer assemblies are adapted to be applied to each other, upon removal of said first face release liner(s) and prior to use, to form a single multi-layer system wherein said first and second layer assemblies are arranged vertically with respect to one another.

17. A transdermal delivery system for delivering systemically pharmaceutically active agents transdermally comprising:
at least one first layer assembly having a first face and a second face and containing a therapeutically effective amount of at least one first systemically pharmaceutically active agent, wherein said first layer assembly has a first release rate for said at least one systemically pharmaceutically active agent; and
a second layer assembly having a first face and a second face and containing a therapeutically effective amount of at least one second systemically pharmaceutically active agent, wherein said second layer assembly has a second release rate for said at least one systemically pharmaceutically active agent;
wherein said first and second systemically pharmaceutically active agents are different;
wherein said first layer assembly is capable of being selectively adhesively adhered to said second layer assembly, which is capable of being selectively adhesively adhered to a user's epidermis;
wherein said first layer assembly and said second layer assembly are separate from each other to maintain characteristics of the assemblies until use;
wherein said first layer assembly comprises (i) a first face release liner adhered to said first face, (ii) a backing layer adhered to said second face; and (iii) a second face release liner adhered to said backing layer;
wherein said second layer assembly comprises (i) a first face release liner adhered to said first face and a (ii) a second face release liner adhered to said second face, and does not include a backing layer; and
wherein said first face of said first and second layer assemblies are adapted to be applied to each other, upon removal of said first face release liner(s) and prior to use, to form a single multi-layer system wherein said first and second layer assemblies are arranged vertically with respect to one another.

18. A method for delivering at least one systemically active compound transdermally to a subject comprising the steps of:
providing a first layer assembly having a first face and a second face and containing a therapeutically effective amount of at least one systemically pharmaceutically active agent and a second layer assembly having a first face and a second face and containing a therapeutically effective amount of at least one systemically pharmaceutically active agent, wherein said first layer assembly is capable of being selectively adhesively adhered to said second layer assembly, which is capable of being selectively adhesively adhered to a user's epidermis,
wherein said first layer assembly comprises (i) a first face release liner adhered to said first face, (ii) a backing layer adhered to said second face; and (iii) a second face release liner adhered to said backing layer and said second layer assembly comprises (i) a first face release liner adhered to said first face and a (ii) a second face release liner adhered to said second face, and does not include a backing layer; and
maintaining said first layer assembly and said second layer assembly separate from each other prior to use;
removing said first face release liner(s) and applying said first face of said first layer assembly and said first face of said second layer assembly to one another to form a single multi-layer system wherein said first and second layer assemblies are arranged vertically with respect to one another;
removing said second face release liner(s), and
applying the single multilayer system to a subject's epidermis.

19. A multi-layer transdermal delivery system comprising:
a first layer assembly having a first face and a second face and containing a therapeutically effective amount of at least one systemically pharmaceutically active agent;
a second layer assembly having a first face and a second face and containing a therapeutically effective amount of at least one systemically pharmaceutically active agent;
a third layer assembly having a first face and a second face and, optionally, containing at least one systemically pharmaceutically active agent;
wherein said first layer assembly is capable of being selectively adhesively adhered to said second layer assembly, which is capable of being selectively adhesively adhered to said third layer assembly, which is capable of being selectively adhesively adhered to a user's epidermis;
wherein said layer assemblies are separate from each other to maintain characteristics of the assemblies until use;
wherein said first layer assembly comprises (i) a first face release liner adhered to said first face, (ii) a backing layer adhered to said second face; and (iii) a second face release liner adhered to said backing layer;
wherein said second and third layer assemblies comprise (i) a first face release liner adhered to said first face and a (ii) a second face release liner adhered to second face, and do not include a backing layer; and
wherein said assemblies are adapted to be applied to each other, upon removal of said first face release liner(s) and prior to use to form a single multi-layer system wherein said first, second and third layer assemblies are arranged vertically with respect to one another.

\* \* \* \* \*

UNITED STATES PATENT AND TRADEMARK OFFICE
CERTIFICATE OF CORRECTION

PATENT NO. : 8,784,874 B2  
APPLICATION NO. : 10/939163  
DATED : July 22, 2014  
INVENTOR(S) : Robert Strauss Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2367 days.

Signed and Sealed this
Eighth Day of September, 2015

Michelle K. Lee
*Director of the United States Patent and Trademark Office*